United States Patent
van Laak et al.

(10) Patent No.: US 6,720,451 B2
(45) Date of Patent: Apr. 13, 2004

(54) METHOD FOR PRODUCING N-METHYL-N'-NITROGUANIDINE

(75) Inventors: Kai van Laak, Köln (DE); Wolfram Sirges, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 24 days.

(21) Appl. No.: 10/169,842

(22) PCT Filed: Jan. 3, 2001

(86) PCT No.: PCT/EP01/00015

§ 371 (c)(1),
(2), (4) Date: Jul. 9, 2002

(87) PCT Pub. No.: WO01/51458

PCT Pub. Date: Jul. 19, 2001

(65) Prior Publication Data

US 2003/0004376 A1 Jan. 2, 2003

(30) Foreign Application Priority Data

Jan. 12, 2000 (DE) .......................................... 100 00 891

(51) Int. Cl.$^7$ .............................................. C07C 291/00
(52) U.S. Cl. ...................................................... 564/108
(58) Field of Search ......................................... 564/108

(56) References Cited

U.S. PATENT DOCUMENTS 6,118,007 A * 9/2000 Ebihara et al. ............. 564/205
6,486,348 B1 * 11/2002 Kern .......................... 564/108

* cited by examiner

*Primary Examiner*—Peter O'Sullivan
(74) *Attorney, Agent, or Firm*—Richard E. L. Henderson; Raymond J. Harmuth

(57) ABSTRACT

The present invention relates to a novel process for the preparation of N-methyl-N'-nitroguanidine by reacting nitroguanidine with aqueous methylamine solution buffered by the addition of inorganic or organic acids.

1 Claim, No Drawings

METHOD FOR PRODUCING N-METHYL-N'-NITROGUANIDINE

This application is a 371 of PCT/EP01/00015 Jan. 3, 2001.

The invention relates to a novel process for the preparation of N-methyl-N'-nitro-guanidine.

It is known that N-methyl-N'-nitroguanidine is obtained if the compound of the formula (A) is firstly nitrated in a customary manner and then, in a second reaction stage, the methylmercapto group is exchanged for methylamine in accordance with the following reaction scheme:

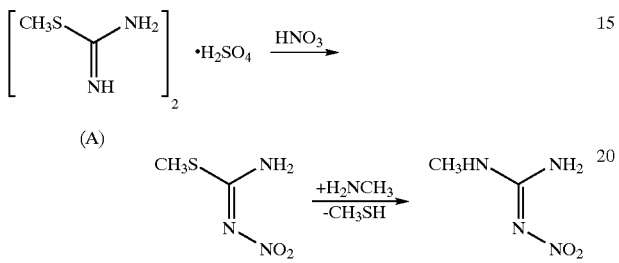

(cf. JACS 1954, 76, 1877).

However, this process has the disadvantage of being a two-stage reaction. Although the yields in both stages are relatively good, the cleaving off of methyl mercaptan, especially when carried out on an industrial scale, presents technical problems.

It is also known that N-methyl-N'-nitroguanidine can be obtained by reacting an alkaline solution (potassium hydroxide) of nitroguanidine with methylamine hydrochloride at 60° C. in accordance with the following reaction scheme:

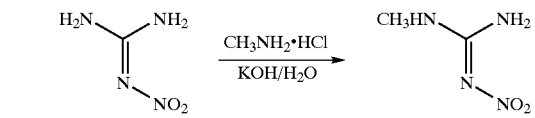

(cf. JACS 1947, 69, 3028).

However, this process has the disadvantage that, to obtain a clean product, at least one to two recrystallizations are necessary to remove inorganic impurities, which leads to losses in yield.

EP 0 798 293 describes a process by which N-methyl-N'-nitroguanidine is obtained by reacting nitroguanidine with aqueous methylamine solution at temperatures between 0° C. and 40° C.

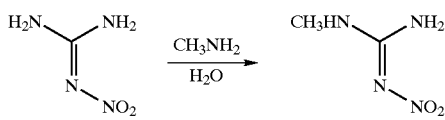

However, in this process the reaction times are very long, meaning that only low space-time yields are achieved. This low space-time yield presents problems when the process is carried out on an industrial scale.

We have now found that N-methyl-N'-nitroguanidine of the formula (I)

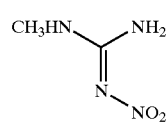

is obtained, when nitroguanidine of the formula (II)

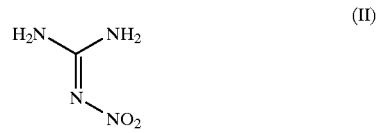

is reacted with aqueous methylamine solution buffered by the addition of inorganic or organic acids.

Surprisingly, using the process according to the invention, N-methyl-N'-nitroguanidine of the formula (I) can be obtained in a simple manner in a very good space-time yield and in high purity. According to the prior art, it was not to be expected that the rate of the reaction can be increased by the addition of acid since, according to JACS 1947, 69, 1947, an excess of KOH is used to obtain methylnitroguanidine.

The reaction according to the invention therefore has the advantage of an increased reaction rate. This leads to the technical advantage of a high space-time yield.

The course of the reaction of the process according to the invention can be outlined by the following reaction scheme:

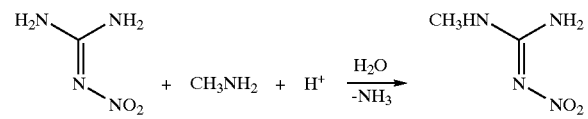

The starting materials nitroguanidine of the formula (II) and methylamine are generally known compounds of organic chemistry.

To buffer the reaction solution, all customary inorganic or organic acids can be used. Examples which may be mentioned are hydrochloric acid, sulphuric acid, nitric acid, phosphoric acid, acetic acid, formic acid and trifluoroacetic acid.

The process according to the invention is carried out in the presence of water as diluent. It is, however, also possible to work in an organic/aqueous system, in which case any customary, water-miscible organic solvent can be used. Examples which may be mentioned are ketones, such as acetone, methyl ethyl ketone or methyl isobutyl ketone; nitrites, such acetonitrile or propionitrile, and alcohols, such as methanol or ethanol.

The reaction temperatures for carrying out the process according to the invention can be varied within a relatively wide range. The process is generally carried out at temperatures between 0° C. and 40° C., preferably between 10°C. and 30°C., particularly preferably between 20° C. and 30° C.

For carrying out the process according to the invention, 1 to 3 mol, preferably 1 to 2 mol, of methylamine are generally used per mole of nitroguanidine of the formula (II).

In the process according to the invention, the pH is generally adjusted to pH=11.0 to 13.0, preferably to pH=11.5 to 13.0, by the addition of acid.

Work-up can be carried out in the usual manner.

The N-methyl-N'-nitroguanidine of the formula (I) to be prepared by the process of the invention can be used as an intermediate for the preparation of biologically active compounds, for example, of insecticides (cf. EP-A 0 376 279 and EP-A 0 428 941).

PREPARATION EXAMPLE

EXAMPLE 1

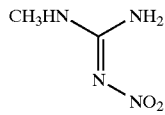

65 g (0.5 mol; 80% strength water-moist) of nitroguanidine are introduced into 75 ml of water and cooled to 5° C. 59 g (0.75 mol) of 40% strength aqueous methylamine solution are metered in. 24.8 g (0.1 mol) of 20% strength sulphuric acid are then metered in. The mixture is heated to 25° C. and stirred for 8 hours at this temperature. The mixture is cooled to 5° C. and filtered, and the filtrate is washed with 50 ml of water.

This gives 51.3 g (87% of theory) of N-Methyl-N'-nitroguanidine of melting point 160° C. with a content of 99% (according to HPLC).

What is claimed is:

1. A process for the preparation of N-methyl-N'-nitroguanidine of the Formula (I)

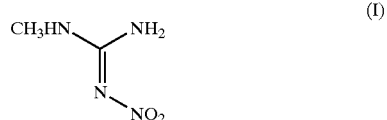

comprising the step of:

reacting nitroguanidine of the Formula (II)

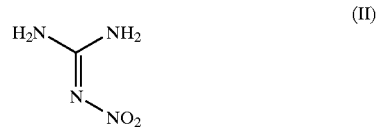

with an aqueous methylamine solution buffered by the addition of an acid selected from the group consisting of an inorganic acid and an organic acid.

* * * * *